United States Patent
Lanier

(10) Patent No.: US 12,336,554 B2
(45) Date of Patent: Jun. 24, 2025

(54) CANNABINOID ACID BEVERAGE

(71) Applicant: CHEMTOR, LP, Lockhart, TX (US)

(72) Inventor: William Lanier, West Jordan, UT (US)

(73) Assignee: Chemtor, LP, Lockhart, TX (US)

( * ) Notice: Subject to any disclaimer, the term of this patent is extended or adjusted under 35 U.S.C. 154(b) by 0 days.

(21) Appl. No.: 18/066,453

(22) Filed: Dec. 15, 2022

(65) Prior Publication Data

US 2023/0124550 A1 Apr. 20, 2023

Related U.S. Application Data

(63) Continuation of application No. PCT/US2021/040139, filed on Jul. 1, 2021.

(60) Provisional application No. 63/047,692, filed on Jul. 2, 2020.

(51) Int. Cl.
*A23L 2/52* (2006.01)
*A23L 33/105* (2016.01)
*A61K 31/192* (2006.01)
*A61K 31/352* (2006.01)

(52) U.S. Cl.
CPC .............. *A23L 2/52* (2013.01); *A23L 33/105* (2016.08); *A61K 31/192* (2013.01); *A61K 31/352* (2013.01)

(58) Field of Classification Search
CPC . A23L 33/105; A23L 2/00; A23L 2/52; A23L 33/10; A23L 2/38; A23V 2250/21; A23V 2250/20; A23V 2200/322; A23V 2200/31; A23V 2002/00; A61K 9/0095; A61K 31/192; A61K 31/352
See application file for complete search history.

(56) References Cited

U.S. PATENT DOCUMENTS

| | | | |
|---|---|---|---|
| 9,907,823 B1 * | 3/2018 | Kuhrts | A61K 9/0014 |
| 2017/0043932 A1 * | 2/2017 | Byun | A23L 2/52 |
| 2018/0193403 A1 | 7/2018 | George et al. | |
| 2019/0177674 A1 * | 6/2019 | Montgomery | C12G 3/055 |
| 2019/0274972 A1 | 9/2019 | Ochoa | |
| 2020/0115663 A1 * | 4/2020 | Worthen | A23L 2/06 |
| 2020/0138072 A1 | 5/2020 | Yucel et al. | |
| 2020/0170944 A1 | 6/2020 | Jackowetz et al. | |
| 2020/0245666 A1 * | 8/2020 | Spall | A23L 2/52 |
| 2020/0375938 A1 * | 12/2020 | Modi | A61K 47/22 |
| 2021/0274814 A1 | 9/2021 | Han | |
| 2022/0257506 A1 * | 8/2022 | Adams | A61K 31/4418 |

FOREIGN PATENT DOCUMENTS

| | | | | |
|---|---|---|---|---|
| KR | 20150042209 A | * | 4/2015 | ............. B65D 17/00 |
| WO | WO 2019/036243 A1 | | 2/2019 | |

OTHER PUBLICATIONS

KR-20150042209-A, English Machine Translation, Apr. 2015 (Year: 2015).*
WHO Guidelines for Drinking Water Quality, pH in Drinking Water, World Health Organization, 2007, pp. 1-2. https://cdn.who.int/media/docs/default-source/wash-documents/wash-chemicals/ph.pdf?sfvrsn=16b10656_4 (Year: 2007).*
Sigma Tween 20 Product Information, retrieved online Jun. 24, 2024, pp. 1-2. (Year: 2024).*
International Search Report and Written Opinion of the International Searching Authority issued by the United States Patent and Trademark Office for International Application No. PCT/US2021/040139 dated Oct. 20, 2021. (8 pages).

* cited by examiner

*Primary Examiner* — Hong T Yoo
(74) *Attorney, Agent, or Firm* — Haynes and Boone, LLP; Michael J. Tobin; Clint Wilkins

(57) ABSTRACT

A cannabinoid acid beverage includes an aqueous solution having a pH of greater than 7 and at least one cannabinoid acid dissolved therein. The cannabinoid acid may include CBDA, THCA, CBGA, CBCA, or combinations thereof. A method of preparing the beverage may include heating the solution to increase the solubility of the cannabinoid acid therein.

17 Claims, No Drawings

CANNABINOID ACID BEVERAGE

CROSS-REFERENCE TO RELATED APPLICATIONS

This application is a continuation of PCT International Patent Application No. PCT/US2021/040139 filed Jul. 1, 2021 and titled "CANNABINOID ACID BEVERAGE", which claims priority to U.S. Provisional Patent Application No. 63/047,692 filed Jul. 2, 2020 and titled "CANNABINOID ACID BEVERAGE", which are hereby incorporated by reference in their entirety.

TECHNICAL FIELD

The present disclosure is related to a beverage comprising one or more cannabinoid acids. More particularly, this disclosure is related to an alkaline beverage including one or more cannabinoid acids dissolved therein.

BACKGROUND

Cannabinoids occur in the hemp plant, *Cannabis sativa*, primarily in the form of cannabinoid carboxylic acids (referred to herein as "cannabinoid acids"). "Neutral cannabinoids" are derived by decarboxylation of their corresponding cannabinoid acids. The more abundant forms of neutral cannabinoids include tetrahydrocannabinol (THC), cannabidiol (CBD), cannabichromene (CBC), and cannabigerol (CBG). Other neutral cannabinoids include, but are not limited to, cannabidivarin (CBDV), cannabichromevarin (CBCV), cannabigerovarin (CBGV), cannabielsoin (CBE), cannabicyclol (CBL), cannabivarin (CBV), cannabitriol (CBT), tetrahydrocannibivarin (THCV), cannabigerol monomethyl ether (CBGM), nabilone, and rimonabant.

Oil extracts from the *Cannabis sativa* plant ("*Cannabis* oil") contain a mixture of cannabinoid acids and neutral cannabinoids along with other naturally occurring components, such as terpenes, terpenoids, sterols (such as phytosterols), triglycerides, alkanes, squalenes, tocopherols, carotenoids, flavonoids, polyphenols, cannflavins, and alkaloids. Although neutral cannabinoids are considered more physiologically active, many of the foregoing components have independent utility. For instance, tetrahydrocannabinolic acid (THCA) and cannabidiolic acid (CBDA) have been used in treating chronic conditions such as ALS, Fibromyalgia, Multiple Sclerosis as well as in patients suffering from neuropathy, pain, anxiety, inflammation, and/or seizures.

DETAILED DESCRIPTION

The following descriptions are provided to explain and illustrate embodiments of the present disclosure. The described examples and embodiments should not be construed to limit the present disclosure.

Recognizing the health benefits (real and perceived) of numerous components of the hemp plant and of alkaline beverages, as well as the solubility of cannabinoid acids in alkaline environments, beverages are presented herein containing various concentrations of cannabinoid acids for human consumption. Due to the solubility of cannabinoid acids at elevated pH, these components can be effectively dissolved into the beverage without the need for remediation techniques such as microencapsulation (see U.S. Patent Application Publication No. 2019/0274972, which is herein incorporated by reference in its entirety).

A beverage according to the present disclosure is an aqueous solution comprising one or more cannabinoid acids dissolved therein. According to one or more embodiments, the aqueous solution may be an alkaline solution having a pH of greater than 7. The alkaline solution is capable of solubilizing one or more cannabinoid acids by deprotonating the cannabinoid acid(s). Accordingly, the pH of the alkaline solution may be selected in view of the $pK_a$ value of the cannabinoid acid(s) to be dissolved therein. Moreover, the pH of the alkaline solution is set such that the beverage is safe for human consumption.

In one or more embodiments, the alkaline solution may have a pH of greater than 7, at least 7.25, at least 7.5, at least 7.75, at least 8, at least 8.25, at least 8.5, at least 8.75, or at least 9. In some embodiments, the alkaline solution has a pH of at most 11, at most 10.5, at most 10.25, at most 10, at most 9.75, at most 9.5, at most 9.25, at most 9, at most 8.75, at most 8.5, at most 8.25, at most 8, at most 7.75, or at most 7.5. The pH of the alkaline solution may range between any logical combination of the foregoing upper and lower limits.

In one or more embodiments, the alkaline solution comprises a basic component, such as sodium bicarbonate, potassium hydroxide, sodium hydroxide, sodium carbonate, potassium bicarbonate, potassium carbonate, any other food-safe pH increasing component, or combinations thereof. In any embodiment, the beverage may be carbonated, non-carbonated, or contain alcohol.

In embodiments of the present disclosure, the addition of acidic cannabinoid acids to the alkaline solution will result in the lowering of the pH and thus may cause the cannabinoid acids to fall out of solution if the resting pH falls below the $pK_a$ of the cannabinoid acids being added. Although the cannabinoids are classified as weak acids, adding numerous cannabinoid acids to the alkaline solution can cause the solution to become unstable wherein all the cannabinoid acids will crash out of solution. This cannot be remedied by simply readjusting the pH after addition of the cannabinoid acids to account for the pH drop. As such, the pH of the alkaline solution must be carefully tailored such that the addition of cannabinoid acids does not drop the pH below the solubility limit of the cannabinoid acids and such that the resultant pH of the beverage, including the alkaline solution and at least one cannabinoid acid, is safe for human consumption. In one or more embodiments, the total cannabinoid content may be 10 mgs, at least 50 mgs, at least 150 mgs, at least 200 mgs, at least 250 mgs, at least 300 mgs, at least 350 mgs, at least 400 mgs, or at least 500 mgs per 30 ml when maintained at room temperature. In some embodiments, the solution may at most contain 1000 mgs, at the most 950 mgs, at the most 900 mgs, at the most 850 mgs, at the most 800 mgs, at the most 750 mgs, at the most 700 mgs, at the most 650 mgs, at the most 600 mgs, or at the most 550 mgs total cannabinoid content per 30 ml when maintained at room temperature (72 degrees Fahrenheit). At increased temperatures, as with freshly brewed coffees and teas, the total cannabinoid concentration can exceed 1000 per 30 ml and this capacity can be further elevated with the use of cream, milk, heavy whipping cream and/or the addition of saturated fats and lipids. Conversely, as is the general rule of temperature and solubility, the total concentration of dissolvable cannabinoids will decrease with decreased temperatures and as such, these beverages should be stored at room temperature until just prior to being served.

In one or more embodiments, the cannabinoid acids comprise CBDA, THCA, cannabigerolic acid (CBGA), cannabidivarinic acid (CBDVA), cannabichromenic acid (CBCA), cannabichromevarinin acid (CBCVA), cannabigerovarinin acid (CBGVA), cannabinolic acid (CBNA), cannabielsoic acid (CBEA), cannabicyclolic acid (CBLA), tetrahydrocannibivarinic acid (THCVA), or combinations thereof.

In some embodiments, the beverage comprises at least 0.001 wt %, at least 0.01 wt %, at least 0.05 wt %, at least 0.1 wt %, at least 0.25 wt %, at least 0.5 wt %, at least 0.75 wt %, at least 1 wt %, at least 1.5 wt %, or at least 2 wt % of cannabinoid acids based on a total weight of the beverage. In some embodiments, the beverage comprises at most 5 wt %, at most 4.5 wt %, at most 4 wt %, at most 3.75 wt %, at most 3.5 wt %, at most 3.25 wt %, at most 3 wt %, at most 2.75 wt %, at most 2.5 wt %, at most 2.25 wt %, at most 2 wt %, at most 1.75 wt %, at most 1.5 wt %, at most 1.25 wt %, at most 1 wt %, at most 0.75 wt %, or at most 0.5 wt % of cannabinoid acids based on a total weight of the beverage. The content of cannabinoid acids may range between any logical combination of the foregoing upper and lower limits. For example, the content of cannabinoid acids may be 0.001 to 5 wt %, 0.1 to 2.5 wt %, or 0.5 to 2 wt %. In some embodiments, the content of cannabinoid acids is equal to a therapeutically effective amount thereof.

According to one or more embodiments, CBDA constitutes at least 50 wt %, at least 60 wt %, at least 70 wt %, at least 75 wt %, at least 80 wt %, at least 85 wt %, at least 90 wt %, at least 95 wt %, or 100 wt % of the cannabinoid acids in the beverage. In one or more embodiments, THCA constitutes at least 50 wt %, at least 60 wt %, at least 70 wt %, at least 75 wt %, at least 80 wt %, at least 85 wt %, at least 90 wt %, at least 95 wt %, or 100 wt % of the cannabinoid acids in the beverage. According to one or more embodiments, CBDA and THCA constitute at least 60 wt %, at least 70 wt %, at least 75 wt %, at least 80 wt %, at least 85 wt %, at least 90 wt %, at least 95 wt %, at least 99 wt %, or 100 wt % of the cannabinoid acids in the beverage.

According to one or more embodiments, CBGA and CBCA constitute at least 0.1 wt %, at least 1 wt %, at least 2 wt %, at least 5 wt %, or at least 10 wt % of the cannabinoid acids in the beverage. In one or more embodiments, CBGA and CBCA constitute at most 50 wt %, at most 25 wt %, at most 15 wt %, at most 10 wt %, at most 5 wt %, at most 2 wt %, or at most 1 wt % of the cannabinoid acids in the beverage.

In one or more embodiments, CBDA, THCA, and CBGA constitute at least 75 wt %, at least 85 wt %, at least 90 wt %, at least 95 wt %, at least 99 wt %, or 100 wt % of the cannabinoid acids in the beverage. In one or more embodiments, CBDA, THCA, CBGA, and CBCA constitute at least 75 wt %, at least 85 wt %, at least 90 wt %, at least 95 wt %, at least 99 wt %, or 100 wt % of the cannabinoid acids in the beverage. In one or more embodiments, CBDA, CBGA, and CBCA constitute at least 75 wt %, at least 85 wt %, at least 90 wt %, at least 95 wt %, at least 99 wt %, or 100 wt % of the cannabinoid acids in the beverage. In one or more embodiments, THCA, CBGA, and CBCA constitute at least 75 wt %, at least 85 wt %, at least 90 wt %, at least 95 wt %, at least 99 wt %, or 100 wt % of the cannabinoid acids in the beverage. In one or more embodiments, CBDA, THCA, and CBCA constitute at least 75 wt %, at least 85 wt %, at least 90 wt %, at least 95 wt %, at least 99 wt %, or 100 wt % of the cannabinoid acids in the beverage.

According to one or more embodiments, the beverage comprises at least two cannabinoid acids. In some embodiments, a weight ratio between a first and second two cannabinoid acid in the beverage is 0.1 to 10, 0.2 to 5, 0.33 to 3, 0.4 to 2.5, 0.5 to 2, 0.67 to 1.5, 0.75 to 1.33, 0.8 to 1.25, 0.9 to 1.1, 1, or any logical combination of the foregoing upper and lower limits. In one or more embodiments, the first cannabinoid acid is CBDA and the second cannabinoid acid is THCA. In one or more embodiments, the first cannabinoid acid is CBDA and the second cannabinoid acid is CBGA. In one or more embodiments, the first cannabinoid acid is THCA and the second cannabinoid acid is CBGA. In one or more embodiments, the first cannabinoid acid is CBDA and the second cannabinoid acid is CBCA. In one or more embodiments, the first cannabinoid acid is THCA and the second cannabinoid acid is CBCA. In one or more embodiments, the first cannabinoid acid is CB GA and the second cannabinoid acid is CBCA.

In some embodiments, the beverage comprises at least three cannabinoid acids. In one or more embodiments, the beverage comprises CBDA, THCA, and CBGA. In some embodiments, the beverage comprises CBDA, CBGA, and CBCA. In some embodiments, the beverage comprises CBDA, THCA, and CBCA. In some embodiments, the beverage comprises THCA, CBGA, and CBCA.

In some embodiments, the beverage does not include any neutral cannabinoids or comprises less than 0.01 wt % or less than 0.001 wt % of neutral cannabinoids based on a total weight of the beverage. In some embodiments, the beverage does not comprise THC, does not comprise CBD, or does not comprise THC nor CBD.

In one or more embodiments, the beverage is transparent or substantially transparent. For instance, the beverage may have a transmittance of at least 95%, at least 98%, at least 99%, or at least 99.9%. In some embodiments, the beverage has a haze of less than 5%, less than 2.5%, less than 1%, less than 0.5%, less than 0.25%, or 0%. In some embodiments, the beverage is optically clear. In other embodiments, the beverage may be colored using a food-safe colorant.

In some embodiments, the beverage may include additives to, for example, improve the flavor of the beverage. Additives may include, but are not limited to, sweeteners such as sucrose, fructose, glucose, erythritol, maltitol, lactitol, sorbitol, mannitol, and/or xylitol, sugar alcohols, polyhydric alcohols, polyalcohols, amino acids, sugar acids, nucleotides, organic acids, inorganic acids, organic salts, inorganic salts, bitter compounds, flavorants, astringent compounds, proteins, surfactants, emulsifiers, gums, antioxidants, colorants, flavonoids, alcohols, polymers or combinations thereof. Other additives may provide a real or perceived heath benefit to the beverage. For example, the beverage may comprise saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols or combinations thereof.

Also provided herein is a packaged beverage, wherein the beverage is as described above. The package may comprise a bottle, can, bag, or any other suitable watertight container. The package may be formed of any food-safe material, such as aluminum or plastic. In some embodiments, the packaged beverage includes a resealable opening.

Also provided herein is a method for preparing the beverage described above. The method includes mechanical mixing of the components of the beverage, and optionally heating the mixture to increase solubility of the components.

Comparative Example 1

50 mgs of high purity (>99% by weight) THCA crystalline powder was added to 250 ml of distilled water at a pH of 6.5. The THCA did not immediately dissolve, not did it dissolve after stirring. The mixture was then heated to 100° C. and the THCA still did not dissolve.

Example 1

The distilled water and THCA from Comparative Example 1 was brought to a pH of 9.5 through the addition of a base and warmed to 40° C. The THCA dissolved into solution and produced a clear aqueous solution. The solution was cooled to room temperature and the solution remained clear (i.e., the THCA remained dissolved in the solution).

Although the present disclosure has been described using preferred embodiments and optional features, modification and variation of the embodiments herein disclosed can be foreseen by those skilled in the art, and such modifications and variations are considered to be within the scope of the present disclosure. It is also to be understood that the above description is intended to be illustrative and not restrictive. Many alternative embodiments will be apparent to those of in the art upon reviewing the above description. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the disclosure.

What is claimed is:

1. A beverage consisting of:
    an aqueous solution consisting of water and a food-safe pH increasing additive; and
    at least one cannabinoid acid dissolved therein.

2. The beverage of claim 1, wherein the food-safe pH increasing additive is selected from the group consisting of sodium bicarbonate, potassium hydroxide, sodium hydroxide, sodium carbonate, potassium bicarbonate, and potassium carbonate.

3. The beverage of claim 1, wherein the at least one cannabinoid acid is selected from the group consisting of acid comprises cannabidiolic acid (CBDA), tetrahydrocannabinolic acid (THCA), cannabigerolic acid (CBGA), and cannabichromenic acid (CBCA).

4. The beverage of claim 1, wherein the at least one cannabinoid acid comprises tetrahydrocannabinolic acid (THCA).

5. The beverage of claim 1, wherein the at least one cannabinoid acid comprises cannabidiolic acid (CBDA) and tetrahydrocannabinolic acid (THCA), and wherein a weight ratio of CBDA to THCA is between 1.1 and 10.

6. The beverage of claim 1, wherein the beverage comprises less than 0.01 wt % of neutral cannabinoids.

7. The beverage of claim 1, wherein the beverage does not comprise tetrahydrocannabinol (THC) nor cannabidiol (CBD).

8. A method of preparing the beverage of claim 1, the method comprising:
    dissolving the at least one cannabinoid acid in the aqueous solution,
    wherein the at least one cannabinoid acid is a crystalline powder.

9. The method of claim 8, further comprising heating the aqueous solution.

10. The method of claim 8, further comprising heating the aqueous solution to at least 40° C. before or after dissolving; and
    after heating and dissolving, cooling the aqueous solution having the at least one cannabinoid acid dissolved therein to room temperature.

11. The method of claim 10, wherein the at least one cannabinoid comprises acid comprises cannabidiolic acid (CBDA), tetrahydrocannabinolic acid (THCA), cannabigerolic acid (CBGA), or cannabichromenic acid (CBCA).

12. The beverage of claim 1, wherein the beverage does not comprise alcohol.

13. The beverage of claim 1, wherein the aqueous solution has a pH of 9.5 or greater.

14. A packaged beverage consisting of:
    a container; and
    a beverage disposed within the container, wherein the beverage consists of:
        an aqueous solution consisting of water and a food-safe pH increasing additive; and
        at least one cannabinoid acid dissolved therein.

15. The packaged beverage of claim 14, wherein the container is a bottle or a can.

16. The packaged beverage of claim 15, wherein the container is aluminum or plastic.

17. The packaged beverage of claim 14, wherein the aqueous solution has a pH of 9.5 or greater.

* * * * *